United States Patent [19]

Halushka et al.

[11] Patent Number: 5,334,369
[45] Date of Patent: Aug. 2, 1994

[54] PLATELET RECEPTOR ANTAGONISTS USEFUL IN DETECTING INTRAVASCULAR PLATELET AGGREGATION

[75] Inventors: Perry V. Halushka, Charleston; Ken M. Spicer, Sullivans Island, both of S.C.; Dale E. Mais, Roachdale, Ind.

[73] Assignee: Medical University of South Carolina, Charleston, S.C.

[21] Appl. No.: 713,726

[22] Filed: Jun. 11, 1991

[51] Int. Cl.$^5$ ............................................. A61K 49/02
[52] U.S. Cl. ............................... 424/1.85; 424/1.45; 424/1.65
[58] Field of Search ........................................ 424/1.1

[56] References Cited

U.S. PATENT DOCUMENTS

| | | | |
|---|---|---|---|
| 4,276,280 | 6/1981 | Akerkar et al. | 424/1.1 |
| 4,520,112 | 5/1985 | Snyder et al. | 436/504 |
| 4,619,823 | 10/1986 | Yokoyama et al. | 424/1.1 |
| 4,656,280 | 4/1987 | Garlick | 424/1.1 X |
| 4,783,330 | 11/1988 | Furie et al. | 424/1.1 |
| 4,976,891 | 12/1990 | Narisada et al. | 260/401 |
| 4,990,326 | 2/1991 | Noujaim et al. | 424/1.1 X |
| 5,002,972 | 3/1991 | Narisada et al. | 514/604 |
| 5,008,409 | 4/1991 | Narisada et al. | 549/463 |
| 5,026,537 | 6/1991 | Daddona et al. | 424/1.1 |

OTHER PUBLICATIONS

Mais, et al., "Radioiododestannylation. Convenient Synthesis of a High Affinity Thromboxane A$_2$/Prostaglandin H$_2$ Receptor Antagonist," *Journal of Labelled Compounds and Radiopharmaceuticals* XXIX:75-79, 1991.
Brenner et al., "Platelet Scintigraphy in Cerebrovascular Diseases," *Eur Neurol* 29:197-201, 1989.
Isaka et al., "Platelet Aggregability and in Vivo Platelet Deposition in Patients with Ischemic Cerebrovascular Disease—Evaluation by Indium-111 Platelet Scintigraphy," *Thrombosis Research* 56:739-749, 1989.
Farlow et al., "Early Image Acquisition After Administration of Indium-111 Platelets in Clinically Suspected Deep Venous Thrombosis," *The American Journal of Cardiology* 64:363-368, 1989.
Ushikubi et al., *Eicosanoids*, vol. 2 (1989) pp. 21-27.
Narisada et al., *J. Med. Chem.* (1988) vol. 31, pp. 1847-1854.
Narisada et al., *J. Org. Chem.* (1989) vol. 54, pp. 5308-5313.
Chemical Abstracts, 111(19):168053d (Nov. 6, 1989) Hanasaki et al., *Biochem. Pharmacol.*, 38(18), pp. 2967-2976.
Chemical Abstracts 111(11):91094h (Sep. 11, 1989) Hanasaki et al., *Biochem. Pharmacol.*, 38(12), pp. 2007-2017.
Chemical Abstracts, 114(1):1107z (Jan. 1, 1991) Ushikubi et al., *Eicosanoids*, 2(1), pp. 21-27.

Primary Examiner—Robert L. Stoll
Assistant Examiner—John M. Covert
Attorney, Agent, or Firm—Needle & Rosenberg

[57] ABSTRACT

This invention provides novel compounds used in a method of determining platelet deposition. These compounds include $^{123}$I-SAP and analogues. Also provided is a method of determining platelet deposition in a subject comprising binding an effective radiolabeled platelet receptor antagonist with a platelet, allowing sufficient time for the platelet to migrate within the subject, and visualizing the radiolabeled platelet in the subject.

10 Claims, No Drawings

PLATELET RECEPTOR ANTAGONISTS USEFUL IN DETECTING INTRAVASCULAR PLATELET AGGREGATION

This invention was made with government support under Grant Number HL 36838 from National Institutes of Health. The United States Government has rights in the invention.

Throughout this application various publications are referenced. The disclosures of these publications in their entireties are hereby incorporated by reference into this application in order to more fully describe the state of the art to which this invention pertains.

BACKGROUND OF THE INVENTION

The blood contains large numbers of platelets, which are not entire cells but small detached cell fragments or "minicells" derived from the cortical cytoplasm of large cells called megakaryocytes. Platelets adhere specifically to the lining of damaged blood vessels, where they help repair breaches and aid in the process of blood clotting.

Unwanted platelet deposition occurs in a variety of disorders. Platelet deposition can lead to thrombosis, tissue ischemia and infarction. For example, intracoronary artery platelet deposition plays an important pathophysiologic role in unstable angina pectoris and reocclusion following percutaneous transluminal coronary artery angioplasty. Additionally, platelet deposition is involved in organ transplant rejection, pulmonary embolus, post vascular grafts and stents. Given this extensive list of disorders, effective detection of intravascular platelet deposition and diagnosis of the associated disorder has long been sought.

Previous techniques that have been employed to visualize platelet deposition have used the non-specific technique of "Indium tagging, Isaka et al., *Thromb. Res.*, 56:739-749 (1989); Farlow, et al., *Am. J. Cardiol.*, 64:363-368 (1989). This technique requires that the platelets first be removed from the patient, separated from the whole blood, labeled with $^{111}$Indium and then reinjected into the patient. The disadvantages of this method are (1) it requires several hours to perform, (2) the platelets may be partially activated during the process which may alter the biodistribution and carries a significant risk of intravascular platelet aggregation to the patient upon reinjection, and (3) the preparation of the platelets and in vitro labeling requires sterile technique and considerable experience. Because of these drawbacks the technique utilizing "Indium has not gained widespread use despite the significant clinical importance of such a detection method.

This invention provides the surprising and effective discovery that a thromboxane $A_2$ receptor antagonist such as $^{123}$I-SAP, can be utilized to visualize disorders associated with intravascular platelet deposition. This method is easy, effective and has the following advantages over the current imaging technique utilizing $^{111}$Indium: (1) since the platelets do not require processing, sterile facilities and additional expertise in the handling of platelets is not required; (2) since processing is not required the method is safer; (3) since the compound is a thromboxane $A_2$ receptor antagonist, there is not a risk of platelet aggregation; and (4) since only the presence of a radiopharmaceutical pharmacy and minimal imaging capabilities are required, the method can be utilized in most hospitals.

SUMMARY OF THE INVENTION

This invention provides novel compounds used in a method of determining platelet deposition. These compounds include $^{123}$I-SAP and analogues. Also provided is a method of determining platelet deposition in a subject comprising binding an effective radiolabeled platelet receptor antagonist with a platelet, allowing sufficient time for the platelet to migrate within the subject, and visualizing the radiolabeled platelet in the subject.

DETAILED DESCRIPTION OF THE INVENTION

This invention provides novel antagonist compounds useful in determining platelet distribution. The synthesis of these compounds requires the $^{123}$I label so that the platelet distribution can be visualized. Minor modifications in the conformations and structure of the compounds that do not affect the ability of the antagonist to bind to a platelet receptor are also included within the scope of the invention. These compounds can be synthesized by the methods set forth in the Examples. Given the synthesis set forth, one skilled in the art can make modifications, additions or variations on the synthesis to produce the claimed compounds.

This invention also provides a method of determining platelet deposition in a subject comprising binding an effective radiolabeled platelet receptor antagonist with a platelet, allowing sufficient time for the platelet to migrate within the subject, and visualizing the radiolabeled platelet in the subject. The general methods taught herein for a thromboxane $A_2$ receptor antagonist are applicable to known or later discovered receptor antagonists. One could apply the general methods set forth herein and radioactively label alternative platelet ligands and visualize platelet deposition. Thus, other proaggregatory receptors such as ADP, collagen, thrombin, epinephrine, IIB/IIIA, platelet activating factor, serotonin and $TXA_2$ could be utilized in a method of detecting platelet receptors. Any antagonist to these receptors which is capable of iodination, for example antibodies which are currently known to be reactive with IIB/IIIA, could be iodinated and used to bind IIB/IIIA, which in turn could be used to detect platelet aggregation. Such receptors could be tested utilizing methods set forth in the Examples. The key feature of the antagonist or antibody is that it cannot significantly interfere with platelet aggregation. In addition, inhibitory receptors such as prostacyclin and $PGE_1$ can be utilized in this invention. From the foregoing it is also clear that antibodies can be utilized in place of an antagonist so long as sufficient aggregation of the labeled platelet occurs. The specific antagonists set forth herein, because of such factors as availability, affinity, and ability to be labeled with $^{123}$I are especially effective in the visualization of platelet deposition.

In the method of determining platelet deposition, the administration of the radiolabeled compounds to the platelets to effect binding can be accomplished by different methods. In one method, the binding occurs by drawing blood from a patient, administering the radioactive platelet receptor antagonist to the blood while in a syringe outside the patient, allowing sufficient time to effect binding with the platelet in the blood and reinjecting the blood into the patient. Preferably, the means to draw the blood from the patient already contains the radiolabeled compounds. Thus, after the platelets have bound the compounds, the radiolabeled platelets can be reinjected in a single step. Such a method minimizes the skill required to administer the compounds.

Alternatively, the radiolabeled platelet receptor antagonist can be administered directly to the blood. In this method the antagonist binds to the platelets in vivo. The platelets are then visualized after they have been deposited. The visualizing is generally accomplished with single photon emission tomography but any suitable detection means can be utilized.

Finally, a method of diagnosing a disorder associated with platelet deposition is provided. The method comprises binding an effective platelet receptor antagonist with a platelet, allowing sufficient time for the platelet to migrate within the subject, and visualizing the radiolabeled platelet in the subject, the presence of intravascular platelet deposition indicating the presence of the disorder. The disorder can be, for example, associated with thrombosis, tissue ischemia, infarction, unstable angina pectoris, percutaneous transluminal coronary artery angioplasty, coronary artery thrombolysis therapy, transient cerebral ischemic attacks, transplantation rejection, pulmonary thrombosis and post vascular grafts and stents.

A pig model is initially utilized for endothelial cell injury and vascular damage. The pig has previously been used as a model for vascular injury and atherosclerosis. Pig blood vessels behave like human vessels in these models of vascular injury. Previous studies in the pig have demonstrated the deposition of $^{111}$In labeled platelets at sites of acute blood vessel wall injury. Thus, the pig has been shown to be a good model for the demonstration of deposition of platelets at the site of vessel wall injury that is directly applicable to humans.

EXAMPLE I

Synthesis and Labeling of $^{123}$-SAP and $^{125}$-SAP $^{123}$I-SAP can be synthesized as follows:
Methyl-7-[(1R,2S,3S,5R)-6,6-dimethy-3-(4-iodobenzenesulfonylamino)-bicyclo[3.1.1]hept-2-yl]-5(Z)-heptenoate IIa Amine methyl ester Ig (50 mg, 180 μmoles) was dissolved in 2 ml of dry toluene and 1.2 equivalents of triethylamine were added. To this mixture was added 59 mg (200 μmoles) of pipsyl chloride and the solution was stirred overnight at room temperature. The toluene was evaporated under a nitrogen stream and the residue taken up in chloroform-methanol (9.5:0.5) and flash chromatographed to yield 84% of a glass solid. DCI-MS:m/z 546(M+H)$^+$, 563(M+NH$_4$)$^+$, 420(M+H−I)$^+$.

Methyl-7-[(1R,2S,3S,5R)-6,6-dimethyl-3-(4-trimethylstannylbenzenesulfonylamino) bicyclo[3,1,1]hept-2-yl]-5(Z)-heptenoate III To a solution of IIa (25 mg, 46 μmoles) in dry dioxane (2 ml) was added hexamethylditin (7.5 mg, 50 μmoles) and 2 mg (3 mole %) of Pd(PPh$_3$)$_4$. The reaction was refluxed for 3 hours, cooled to room temperature, filtered through celite and the residue evaporated to dryness under a nitrogen stream. Flash chromatography was carried out with silica gel permeated with pyridine and eluted with chloroform-methanol (9.5:0.5) to give 62% yield of the trimethyltin derivative III. DCI-MS:m/z 584(M+H)$^+$, 601(M+NH$_4$)$^+$, 520(M+H-Sn(CH$_3$)$_3$)$^+$. This product was dissolved in dry hexane at a concentration of 2 mM and stored at −20° C. under an argon atmosphere. This served as the precursor for introduction of $^{125}$I.

7-[(1R,2S,3S,5R)-6,6-dimethyl-3-(4-iodobenzenesulfonylamino) bicyclo[3.1.1]hept-2-yl]-5(Z)-heptenoic acid (I-SAP) IIb 10 mg (18 μmoles) of methyl ester IIa was quantitatively converted to the free acid IIb by THF:0.2N LiOH (1:1) at room temperature for 15 hours. DCI-MS:m/z 532(M+H)$^+$, 549 (M+NH$_4$)$^+$, 406 (M+H-I)$^+$.

7-[1R, 2S, 3S, 5R)-6,6-dimethyl-3-(4-[$^{125}$I]-iodobenzenesulfonylamino) bicyclo [3.1.1]hept-2-yl]-5(Z)-heptenoic acid ([$^{125}$I ]-I-SAP) IV 2 nmoles of III was evaporated under argon and 25 ul of MeOH added. To this was added 1 mCi [$^{125}$I]-NaI followed by 10 ul of chloramine-T dissolved in 200 mM phosphate buffer at pH 7.5 (5 mg chloramine-T/ml). After 4 minutes, 10 ul of THF and 10 ul of 2N LiOH (in water) was added. The hydrolysis of the methyl ester was complete after 1 hour. The reaction mixture was injected onto a Whatman ODS-3 reverse phase column and the product eluted with 68% MeOH-32% 0.1M NH$_4$Ac. Under these conditions, the product eluted at 9-10 minutes and comigrated with I-SAP by HPLC and TLC. The yield based on starting [$^{125}$I] was 69+/−5% (N=4). A theoretical specific activity of 2200 Ci/mmole can be assigned since $^{125}$I-SAP can be separated from starting material. $^{125}$I can be substituted for $^{125}$I in this synthesis.

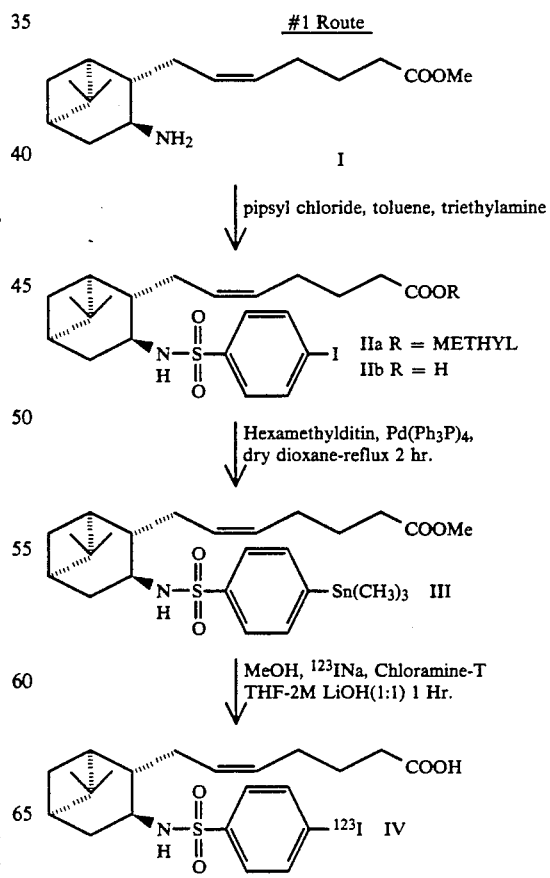

EXAMPLE II
Synthesis of $^{123}$I-SAP Analogs
#2 Route
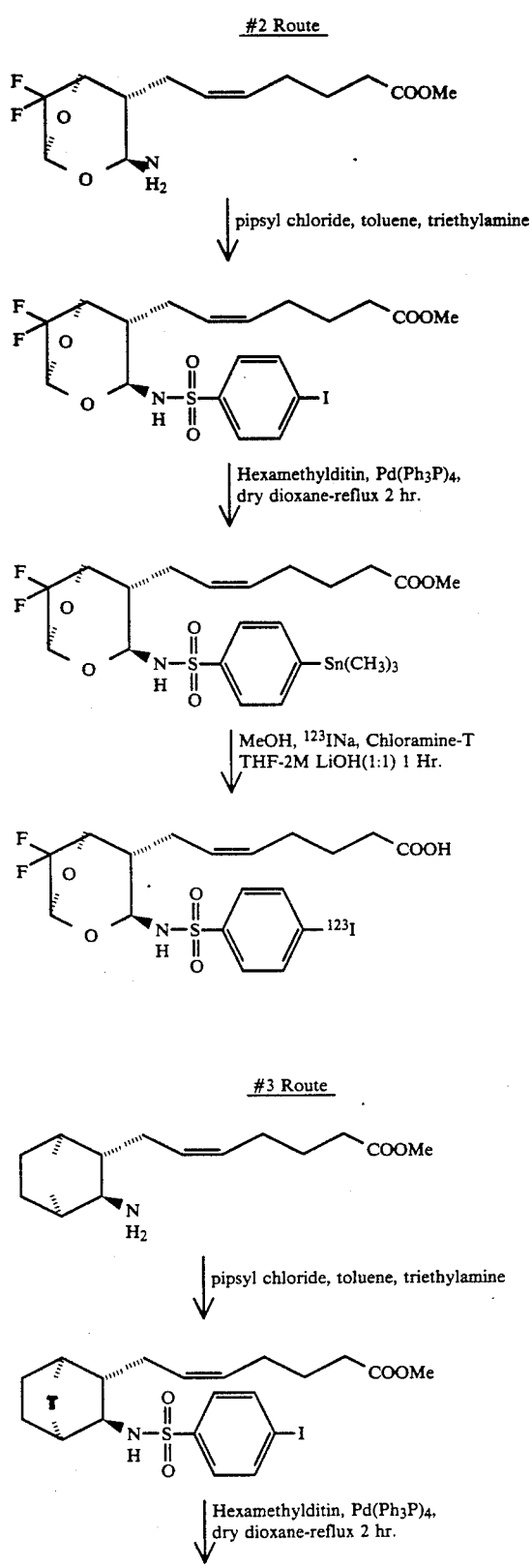
#3 Route
-continued
#3 Route
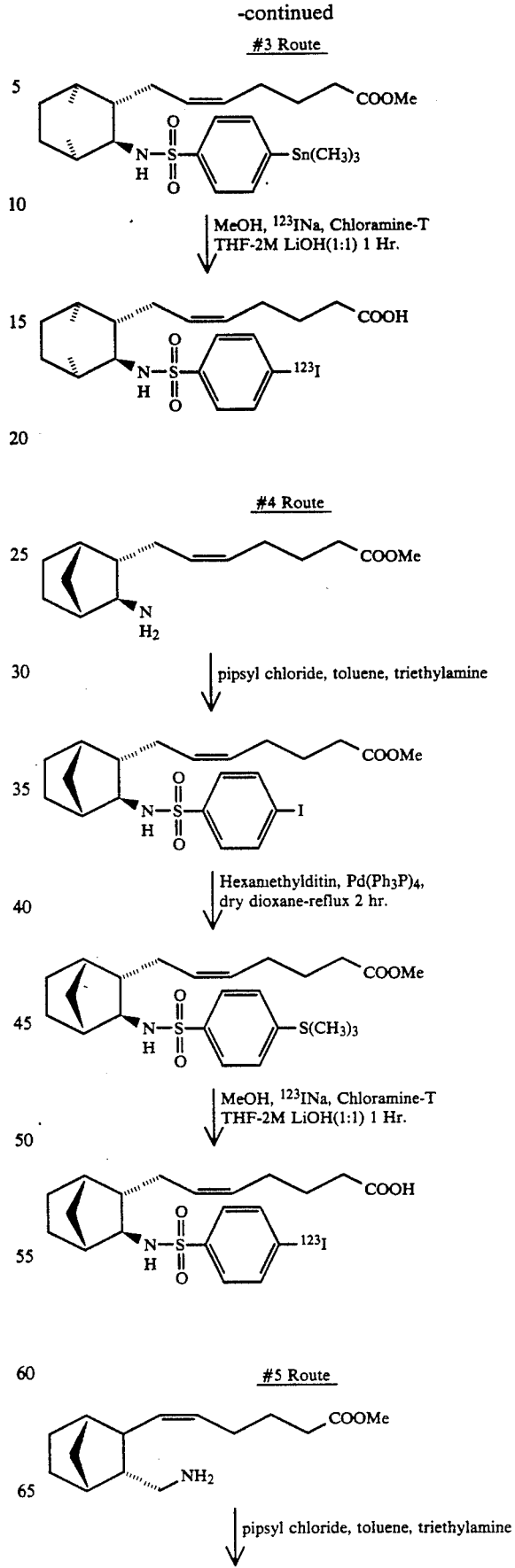
#4 Route
#5 Route

5 Route
6 Route
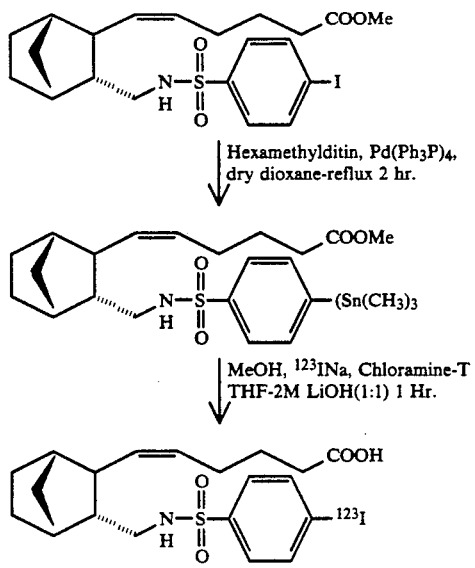
6 Route
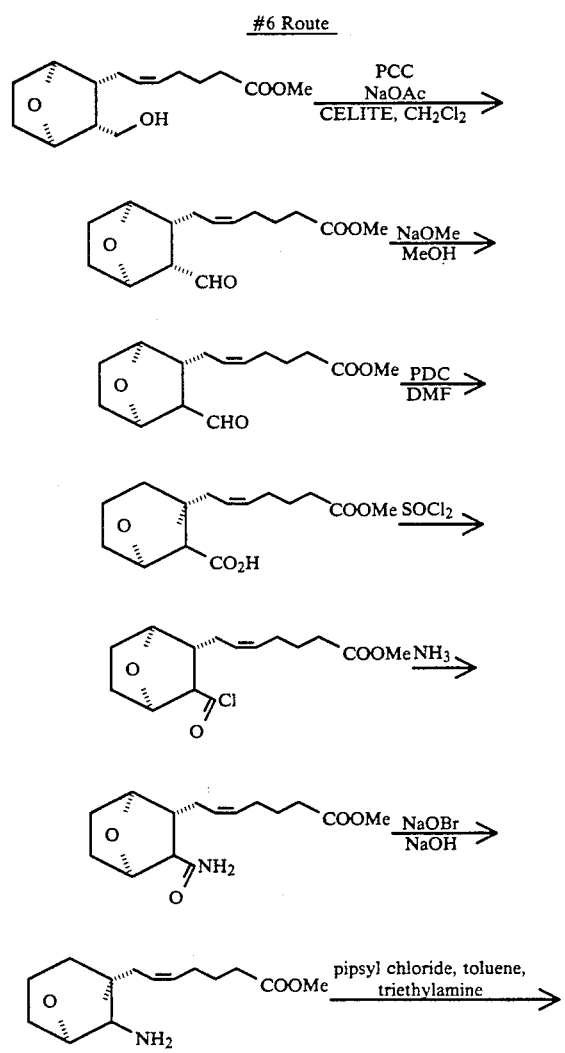
7 Route
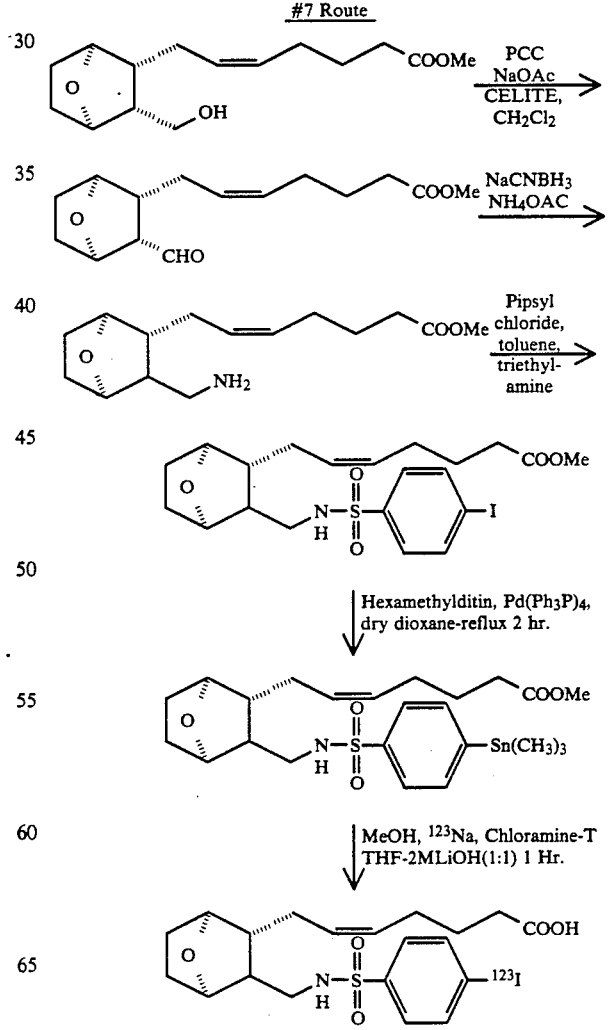

EXAMPLE III

Determining the Affinity and $B_{max}$ (Maximum Number of Binding Sites) for I-SAP in Pig Platelets It has already been well established that pig blood vessels serve as a useful model for human blood vessels. Previous studies have demonstrated that pig platelets behave in a manner similar to human platelets. However, it has not been unequivocally established that pig platelet thromboxane $A_2$ receptors behave exactly like human platelet thromboxane $A_2$ receptors. To demonstrate this, washed pig platelets are prepared using the methods previously described for preparation of washed human platelets, Morinelli et al. (1989). Briefly, blood is collected via venipuncture into a solution containing indomethacin (10 $\mu$M final concentration) and EDTA (5 mM final concentration). Platelet rich plasma is prepared by centrifugation at 150x gravity for 15 minutes. The platelet rich plasma is removed and centrifuged at 1500x gravity for 15 minutes. The resulting platelet pellet is resuspended in HEPES(25 mM)/NaCl (100 mM)/glucose (5 mM), pH 7.4 to a final platelet count of $1 \times 10^8$ platelets/ml.

The binding characteristics of $^{125}$I-SAP to pig platelets are also determined using previously described methods for the binding of I-SAP to washed human platelets Naka et al. Briefly, the assay consists of 100 $\mu$l of the platelet suspension, $^{125}$I-SAP (25,000 cpm), additional concentrations of I-SAP in a total volume of 200 $\mu$l. The mixture is incubated for 30 minutes at 37° C. The mixture is then filtered and washed 4 times with ice cold buffer. The amount of $^{125}$I-SAP bound to the washed platelets is determined by counting them in a gamma spectrometer.

Using these methods, pig platelet thromboxane $A_2$ receptors demonstrated an affinity for $^{125}$I-SAP similar to that found for human platelet thromboxane $A_2$ receptors.

EXAMPLE IV

Determining Maximal Binding Time of I-SAP to Pig Platelets in Whole Blood

To reach equilibrium, the binding of a platelet receptor antagonist (e.g., antagonist) to its receptor requires a finite period of time. For I-SAP in washed human platelets, it takes approximately 15 minutes to reach equilibrium at 37° C. Thus, in human samples, 15 minutes can be utilized. In order to maximize the binding of I-SAP to the platelet thromboxane $A_2$ receptor, the time necessary for I-SAP to bind to pig platelets in whole blood can be determined before conducting the whole animal experiments.

$^{125}$I-SAP or $^{123}$I-SAP can be utilized. Pig blood (10 to 15 ml) is drawn into a syringe containing acid citrate-dextrose (pH 6.5) and 200 to 500 $\mu$Ci of $^{123}$I-SAP or $^{125}$I-SAP in the presence or absence of a large molar excess of a thromboxane $A_2$ receptor antagonist. The tube containing the large molar excess serves to establish the nonspecific binding of I-SAP. The tube of blood is gently rocked. At intervals of 1 minute up to 30 minutes, 10 $\mu$l aliquots are removed and filtered using previously described techniques for the separation of platelet receptor antagonist bound to the receptor from free platelet receptor antagonist, Naka et al., supra. 200 to 500 $\mu$Ci of $^{123}$I-SAP is utilized since that is a dose of $^{123}$I-SAP which is injected into both pigs and patients.

After the optimal time to reach equilibrium is determined an additional series of standard experiments are performed to establish that the predominate amount of specific binding is to platelets. Upon reaching equilibrium, whole blood is centrifuged to obtain platelet rich plasma and packed red blood cells. Aliquots of the platelet rich plasma and packed red blood cells are counted in a gamma counter and the amount of radioactivity in the two fractions is determined. This helps to further establish that the binding of $^{123}$I-SAP is to the platelet thromboxane $A_2$ receptor.

These experiments allow one to establish the optimal time and loading conditions for I-SAP binding to platelets and can allow the optimal labeling of pig platelets in vivo.

EXAMPLE V

Determining the Optimal Dose of $^{123}$I-SAP for Imaging Platelet Deposition in Carotid Arteries Damaged a Balloon Catheter in Pigs In some experiments $^{111}$Indium labeled platelets are used instead of $^{123}$I-SAP to compare the results obtained with $^{123}$I-SAP with the current standard for imaging platelets.

Pigs are initially anesthetized using a combination of ketamine (33 mg/kg) and acepromazine (15 mg/kg) followed by pentobarbital (25–50 mg/kg). They are treated intravenously with aspirin (30 mg/kg) immediately after induction of anesthesia. The pigs are treated with aspirin to inhibit platelet thromboxane $A_2$ formation. This is done to minimize competition of $^{123}$I-SAP with the thromboxane $A_2$ receptor and maximize the amount of $^{123}$I-SAP bound to the receptor. The left femoral artery is exposed and a balloon catheter is inserted in the artery and passed forward to the left carotid artery. Its position is confirmed angiographically. The injury is induced by inflating the balloon and drawing it back and forth through the carotid artery using the method of Steele et al., Circ. Res. 57:105–112 (1985).

Platelets are labeled with I-SAP using the following method. $^{123}$I-SAP is loaded into a syringe containing acid citrate dextrose (6:1 ml). The total doses injected are 200, 350 and 500 $\mu$Ci. Platelets are also labeled with $^{111}$In(500 $\mu$Ci) using the previously described methods of Isaka et al., *Thromb. Res.*, 56:739–49 1989. A heparin lock (19 gauge) is inserted into a peripheral vein and 10 to 15 cc of blood is drawn into the syringe. An aliquot of blood is taken and a platelet count determined. The blood remains in the syringe for the optimal time for maximal binding established in examples described herein and is reinjected into the systemic circulation. Prior to injection an aliquot 100 $\mu$l is removed and spun to separate the platelets from the red and white blood cells. A platelet count is performed and the amount of $^{123}$I-SAP associated with the platelets is determined. The cpm/platelet is calculated and used to determine the number of platelets adhering to the injured carotid vessels. The left and right carotid arteries of the pigs are imaged using a computer based gamma camera. Dynamic imaging is conducted from 0 to 30 minutes, then static imaging is carried out at 60, 120, 150 and 180 minutes after reinjection of the labeled platelets. Longer periods of time can also be tested. The right carotid artery is used as a control for the damaged left carotid artery. The radioactivity associated with each carotid artery is determined at each time point and ratios (injured/control) (cpm/pixel) are calculated. At each one of these time intervals a 5 cc aliquot of blood is removed. This is centrifuged to separate the formed elements of the blood from the plasma. The amount of radioactivity associated with the plasma and formed elements of the blood is determined. This data provides the opportunity to determine if $^{123}$I-SAP is dissociating from the receptor with time and circulating in the plasma. At the end of the imaging period, the pigs are sacrificed using an overdose of anesthetic. After that the carotid arteries are removed and the amount of radioactivity associated with them is determined as set forth in Example VI.

One potential problem is that the $^{123}$I-SAP dissociates from the platelet receptor over a period of time which will limit the useful time that the imaging can take place. This can be determined in part by virtue of measuring the amount of radioactivity associated with the plasma and platelets during the imaging periods. Another potential problem is that an insufficient amount of radioactivity adheres at the site of the injured vessel. To control these possibilities, we conduct experiments with $^{111}$In labeled platelets which have already been shown to be able to image platelet deposition at the sites of blood vessel wall injury.

These studies are performed by loading platelets with $^{123}$I-SAP in whole blood in a syringe. This allows for the maximum loading of the platelets. Subsequent experiments can load the platelets while in the circulation by intravenously injecting $^{123}$I-SAP. This has the advantage of not removing blood for even a short period of time.

EXAMPLE VI

Quantitating the Amount of $^{123}$-SAP Deposited in the Injured and Contralateral Carotid Arteries of Pigs by Direct Radioactive Counting of the Carotid Arteries As a further assessment of the amount of platelet deposition on the injured vessels, the vessels are removed from the pig and counted. This data is valuable in assessing how many platelets adhered to the vessels and also the sensitivity of the imaging.

After the pigs are sacrificed with an overdose of anesthetic, the carotid arteries are exposed and perfused with physiologic saline to remove loosely adherent cells and then the vessels are removed and counted in a gamma counter. The same length of carotid artery is removed from both sides.

One potential problem is that the platelets are loosely adherent to the vessels and are easily washed off during the perfusion of the vessel. If that occurs, it may appear that fewer platelets were adherent. One control for this is to perfuse with a fixative solution which will fix the platelets to the vessel wall and preclude this possibility. If it appears that no platelets are adherent to the vessel walls after perfusion, then perfusing with a fixative solution can be utilized.

The $^{123}$I-SAP method effectively binds to pig platelets and is effective in imaging platelet deposition in injured arteries.

EXAMPLE VII:

Detecting Platelet Aggregation in Human Subjects

The optimal dose per weight of the subject for $^{123}$I-SAP as determined in Example V is quantitated for the human subject. Blood drawn from the human subject is bound to $^{123}$I-SAP for 15 minutes as set forth in Example IV. The blood is then reinjected into the human subject for the optimal time as determined in Example V. Alternatively, the $^{123}$I-SAP can be directly injected into the bloodstream. After the optimum circulation time for deposition is determined as in Example V, the subject is then imaged using a computer-based gamma camera. The site of platelet deposition is visualized and the disorder diagnosed based on this distribution.

What is claimed is:

1. A method of determining platelet deposition in a subject comprising binding an effective radiolabeled thromboxane A$_2$ receptor antagonist with a platelet, allowing sufficient time for the platelet to migrate within the subject, and visualizing the radiolabeled platelet in the subject.

2. The method of claim 1, wherein the thromboxane A$_2$ receptor antagonist is a compound having the following structure:

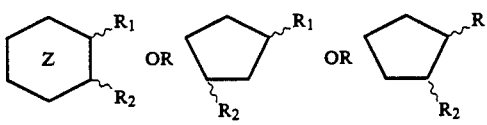

R$_1$ and R$_2$ are either $\alpha$ or $\beta$ to the ring system and are considered to be any compound with R$_1$ =

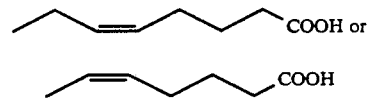

and R$_2$ =

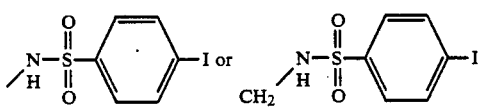

and Z =

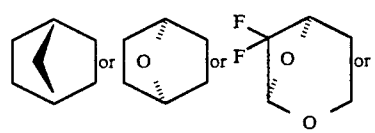

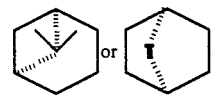

3. The method of claim 2, wherein the thromboxane A$_2$ receptor antagonist is a compound having the structure:

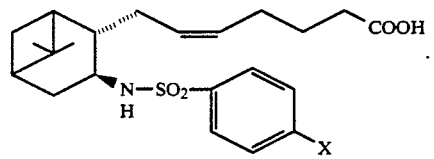

4. The method of claim 1, wherein the radioactive label is $^{123}$I.

5. The method of claim 1, wherein the radioactive platelet receptor antagonist is administered directly to the blood to effect binding with the platelet.

6. The method of claim 1, wherein the binding occurs by drawing blood from a patient, administering the radioactive platelet receptor antagonist to the blood outside the patient, allowing sufficient time to effect binding with the platelet in the blood and reinjecting the blood into the patient.

7. The method of claim 6, wherein the blood is drawn into a syringe containing the radioactive platelet receptor antagonist.

8. The method of claim 1, wherein the visualizing is accomplished with single photon emission computed tomography.

9. A method of diagnosing a disorder associated with platelet deposition comprising binding an effective radiolabeled thromboxane $A_2$ receptor antagonist with a platelet, allowing sufficient time for the platelet to migrate within the subject, and visualizing the radiolabeled platelet in the subject, the presence of intravascular artery platelet deposition indicating the presence of the disorder.

10. The method of claim 9, wherein the disorder is or is associated with a member selected from the group of thrombosis, tissue ischemia, infarction, unstable angina pectoris, percutaneous transluminal coronary artery angioplasty, coronary artery thrombolysis therapy, transient cerebral ischemic attacks, transplantation rejection, pulmonary thrombosis, and post vascular grafts and stents.

* * * * *

UNITED STATES PATENT AND TRADEMARK OFFICE
CERTIFICATE OF CORRECTION

PATENT NO. : 5,334,369
DATED : Aug. 2, 1994
INVENTOR(S) : Halushka et al.

It is certified that error appears in the above-indentified patent and that said Letters Patent is hereby corrected as shown below:

Column 5, line 50, the formula should appear as follows:

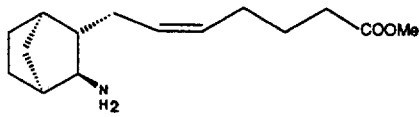

Column 5, line 60, the formula should appear as follows:

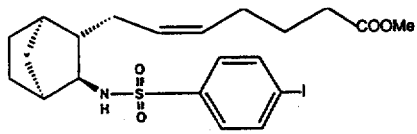

Column 6, line 5, the formula should appear as follows:

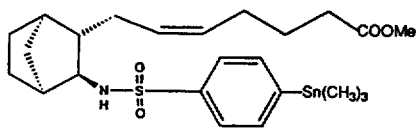

Column 6, line 14, the formula should appear as follows:

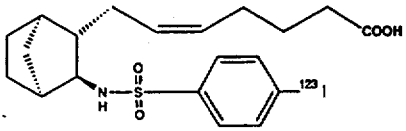

UNITED STATES PATENT AND TRADEMARK OFFICE
CERTIFICATE OF CORRECTION

PATENT NO. : 5,334,369
DATED : Aug. 2, 1994
INVENTOR(S) : Halushka et al.

It is certified that error appears in the above-indentified patent and that said Letters Patent is hereby corrected as shown below:

(continued from previous page)

Column 7, line 45, the formula should appear as follows:

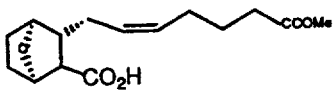

Column 7, line 63, the formula should appear as follows:

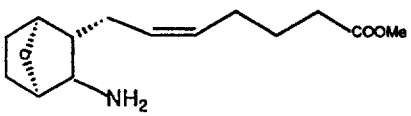

Column 12, line 45, the right-hand formula after the word "or" should appear as follows:

Signed and Sealed this

Fourteenth Day of March, 1995

Attest:

BRUCE LEHMAN

Attesting Officer

Commissioner of Patents and Trademarks